United States Patent [19]
Harada et al.

[11] Patent Number: 5,599,763
[45] Date of Patent: Feb. 4, 1997

[54] ABSORBENT MATERIAL, ABSORBENT BODY, AND METHOD FOR PRODUCTION THEREOF

[75] Inventors: Nobuyuki Harada, Suita; Kazumasa Kimura, Ikoma; Tadao Shimomura, Toyonaka, all of Japan

[73] Assignee: Nippon Shokubai Co., Ltd., Osaka, Japan

[21] Appl. No.: 283,181

[22] Filed: Aug. 3, 1994

Related U.S. Application Data

[62] Division of Ser. No. 752,054, Aug. 29, 1991, Pat. No. 5,368,918.

[30] Foreign Application Priority Data

| Aug. 30, 1990 | [JP] | Japan | 2-226679 |
| Aug. 30, 1990 | [JP] | Japan | 2-226680 |
| Aug. 30, 1990 | [JP] | Japan | 2-226681 |

[51] Int. Cl.$^6$ .................................................. B01J 20/22
[52] U.S. Cl. ..................... 502/402; 428/219; 428/403; 428/207
[58] Field of Search .................... 502/402; 428/219, 428/283, 288, 403, 407

[56] References Cited

U.S. PATENT DOCUMENTS

| 3,819,514 | 6/1974 | Clampitt et al. | 210/40 |
| 3,901,236 | 8/1975 | Assarsson et al. | 128/284 |
| 4,235,237 | 11/1980 | Mesek et al. | 128/284 |
| 4,354,487 | 10/1982 | Oczkowski et al. | 128/156 |
| 4,497,710 | 2/1985 | Wagu et al. | 210/635 |
| 4,784,892 | 11/1988 | Storey et al. | 428/286 |
| 4,885,204 | 12/1989 | Bither et al. | 428/286 |
| 4,897,297 | 1/1990 | Zafiroglu | 428/286 |
| 5,195,999 | 3/1993 | Harada et al. | 604/368 |
| 5,368,918 | 11/1994 | Harada et al. | 428/219 |

FOREIGN PATENT DOCUMENTS

| 0192216 | 8/1986 | European Pat. Off. . |
| 0210968 | 2/1987 | European Pat. Off. . |
| 0317058 | 5/1989 | European Pat. Off. . |
| 0339461 | 11/1989 | European Pat. Off. . |
| 0359615 | 3/1990 | European Pat. Off. . |
| 2153358 | 5/1973 | France . |
| 2513895 | 4/1983 | France . |
| 58-8175 | 1/1983 | Japan . |
| 58-163438 | 9/1983 | Japan . |
| 63-122452 | 5/1988 | Japan . |
| 601012 | 6/1978 | Sweden . |
| 2176815 | 1/1987 | United Kingdom . |
| 2214201 | 8/1989 | United Kingdom . |

OTHER PUBLICATIONS

"Pulp, Synthetic", vol. 19, pp. 420–423 (yr unavailable).
Terence W. Rave, "Synthetic Pulp", Chemtech, Jan. 1985, pp. 54–63.

*Primary Examiner*—Anthony McFarlane
*Attorney, Agent, or Firm*—Burns, Doane, Swecker & Mathis, L.L.P.

[57] ABSTRACT

An absorbent material produced by mixing 100 parts by weight of an absorbent polymer with 1 to 80 parts by weight of synthetic pulp in the presence of 1 to 40 parts by weight of water, an absorbent body produced by mixing 100 parts by weight of an absorbent polymer with 1 to 80 parts by weight of synthetic pulp in the presence of 1 to 40 parts by weight of water, dry mixing the resultant mixture with 10 to 1,000 parts by weight hydrophilic fibers based on 100 parts by weight of said absorbent polymer, pneumatically molding the resultant mixture in the form of web, and thermally compressing the resultant web to a density in the range of from 0.1 to 1.0 g/cm$^3$, and a method for production thereof.

23 Claims, 2 Drawing Sheets

F I G. 1
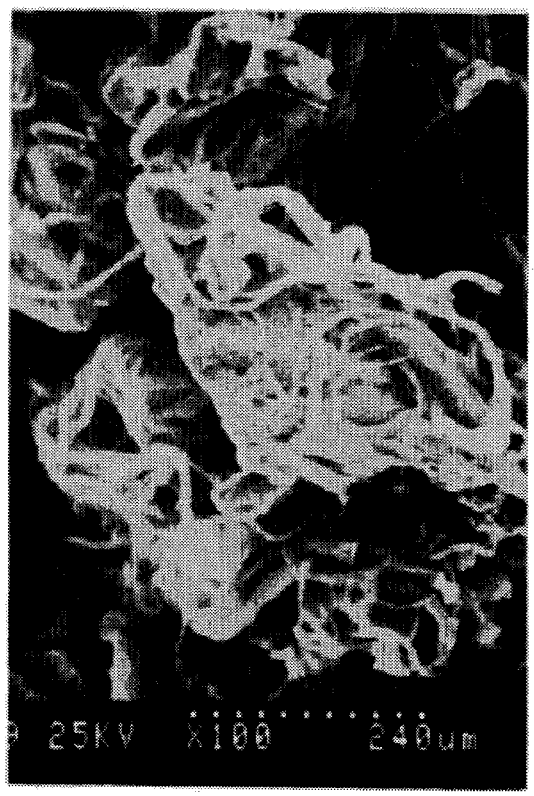

ABSORBENT MATERIAL, ABSORBENT BODY, AND METHOD FOR PRODUCTION THEREOF

This application is a divisional of application Ser. No. 07/752,054, filed Aug. 29, 1991, now U.S. Pat. No. 5,368,918.

BACKGROUND OF THE INVENTION

1. Field of the Invention

This invention relates to an absorbent material, an absorbent body, and a method for the production thereof. More particularly, it relates to an absorbent material which, in its independent form, possesses excellent absorbing characteristic and molding property and, in the form incorporated in a fiber matrix, manifests preeminently excellent effect and to a method for the production thereof. It further relates to an absorbent body which is soft, stable, and incapable of causing exfoliation of an absorbent polymer and a method for the production thereof.

2. Description of the Prior Art

Heretofore, absorbent polymer particles coated with a hydrophilic cellulose and an absorbent article containing them have been disclosed U.S. Pat. No. 3,901,236 and JP-A-58-163,438(1983)). As means aimed at enabling an absorbent article to manifest improved strength while in a wet state, a method which comprises dry mixing thermoplastic fibers into the absorbent article (JP-A-56-89,839(1981), JP-A-58-8,175(1983), and JP-A-63-122,452(1988)). and an absorbent material having a hydrophobic fiber web partly embedded in an absorbent polymer and an absorbent article using the absorbent material U.S. Pat. Nos. 4,354,487 and 4,235,237 have been taught.

In the case of the method mentioned above, however, an absorbent article to be obtained by dispersing an absorbent polymer coated with a hydrophilic cellulose in a hydrophilic fiber matrix exhibits an improved ability for absorption of a liquid as compared with the absorbent polymer used in its independent form. The absorbent article wetted with the absorbed liquid, however, is deficient in strength. Particularly on account of the molding strength, the absorbent polymer concentration in the matrix has its own limit.

In the case of the absorbent material mentioned above, the incorporation of a thermoplastic fiber by dry mixing results in improving the stability of the web in the wet form and yet induces no sufficient solidification of the absorbent polymer. When the absorbent material is compressed to a high degree enough to ensure solidification of the absorbent polymer, the absorbent article consequently obtained is unduly rigid and the absorbent article's capacity for absorption is unduly low because of the inevitable decrease in the content of the absorbent polymer's voids available for swelling within the web. Thus, an attempt to increase the absorbent polymer concentration in the web or densify the absorbent polymer is difficult to fulfil. The partial embedment of the fiber web in the absorbent polymer indeed improves the wet strength and the molding strength of the produced absorbent material and yet induces the fibers to restrict the swelling of the absorbent material. Moreover, it has the disadvantages that the absorbing characteristic is inferior, the swelled absorbent polymer exhibits unduly low gel strength, and the production of the absorbent material consumes much time and labor.

An object of the present invention, therefore, is to provide a novel absorbent material, an absorbent body, and a method for the production thereof.

Another object of the present invention is to provide an absorbent material which, in the independent form, possesses excellent absorbing characteristic and molding property and, in the form incorporated in a fiber matrix, manifests preeminently excellent effects (wet stability, shape-retaining property, dispersibility, and absorbing characteristic) and a method for the production thereof.

Yet another object of the present invention is to provide a thin absorbent body which is soft, stable in the wet form (shape-retaining property), and incapable of causing exfoliation of an absorbent polymer and which is made chiefly of an absorbent polymer and enabled to manifest a highly satisfactory absorbing property and a method for the production thereof.

SUMMARY OF THE INVENTION

These objects of the present invention are accomplished by a method for the production of an absorbent material characterized by mixing 100 parts by weight of an absorbent polymer with 1 to 80 parts by weight of synthetic pulp in the presence of 1 to 40 parts by weight of water.

These objects are further accomplished by an absorbent material comprising physical mixture of 100 parts by weight of an absorbent polymer and 1 to 80 parts by weight of synthetic pulp, wherein the absorbent polymer surface is coated with synthetic pulp.

These objects are also accomplished by a method for the production of an absorbent body characterized by mixing 100 parts by weight of an absorbent polymer with 1 to 80 parts by weight of synthetic pulp in the presence of 1 to 40 parts by weight of water, combining the resultant mixture with 10 to 1,000 parts by weight of hydrophilic fibers based on 100 parts by weight of the absorbent polymer, and heat-treating the resultant web.

These objects are further accomplished by an absorbent body comprising a coherent web of 10 to 1,000 parts by weight of hydrophilic fibers and 100 parts by weight of an absorbent polymer particles held within the web, the absorbent polymer particles being combined with the hydrophilic fibers as the fusion with 1 to 80 parts by weight of the dispersed absorbent polymer particles.

These objects are further accomplished by a method for the production of an absorbent, body characterized by comprising (a) a step of mixing 100 parts by weight of an absorbent polymer with 1 to 80 parts by weight of synthetic pulp in the presence of 1 to 40 parts by weight of water, (b) a step of dry mixing the resultant mixture from the step of (a) with 10 to 1,000 parts by weight of hydrophilic fibers based on 100 parts by weight of the absorbent polymer, (c) a step of pneumatically molding the resultant mixture from the step of (b) in the form of a web, and (d) a step of thermally compressing the web to a density in the range of from 0.1 to 1.0 g/cm³.

These objects are also accomplished by an absorbent body comprising a web of 10 to 1,000 parts by weight of hydrophilic fibers and 100 parts by weight of absorbent polymer particles uniformly dispersed and held within the web, the particles being combined with the fibers as the fusion with 1 to 80 parts by weight of synthetic pulp occurs in the surface regions of the particles, and the web being compressed to a density in the rankle of from 0.1 to 1.0 g/cm³.

The absorbent material which is obtained by the present invention possesses the following characteristic features.

When this absorbent material is used in its independent form:

(1) It avoids producing fish-eyes because the particles thereof are coated with synthetic pulp.

(2) It requires only a simple step of heating to produce a shaped article by the combination of absorbent polymer particles. The shaped article may be so produced that the particles will be combined as dispersed with voids. The shaped article thus produced, therefore, excels in the wicking property.

(3) It has a smaller bulk density than an equivalent bulk formed solely of particles and, therefore, possesses a characteristic property of being easily dispersed uniformly in other matrix (such as, for example, ground pulp).

When the absorbent material of this invention is incorporated in a fiber matrix and the resultant composite is subjected to a heat treatment:

(4) It enables the produced absorbent body to exhibit improved strength while in a dry form or in a wet form.

(5) It enables the produced absorbent body to increase the absorbent material concentration thereof to a level falling in the heretofore unattainable range without a sacrifice of the efficiency of absorption of the absorbent polymer.

(6) Since the fusion with the synthetic pulp occurs in the surface regions of the thoroughly dispersed absorbent polymer particles and this fusion occurs in such a manner as to envelope the particles, the absorbent material while absorbing a liquid prevents the absorbent polymer particles from forming a gel block, allows the swelled absorbent polymer particles to manifest an increased gel strength, and precludes exfoliation of absorbent polymer particles.

(7) It enables the produced arbsorbent body to be notably improved in wicking property, capacity for absorption, and elasticity.

The absorbent body to be obtained by the present invention enjoys the following characteristic features.

(1) It exhibits high strength while in the dry form and in the wet form and it is soft.

(2) Since the fusion with the thermoplastic fibers occurs in the surface regions of the thoroughly dispersed absorbent polymer particles, the absorbent body while absorbing a liquid prevents the absorbent polymer particles from producing a gel block and enables the swelled absorbent polymer particles to acquire improved gel strength.

(3) It acquires notable improvement in wicking property, capacity for absorption, and elasticity.

(4) The absorbent commodities using the absorbent body of the present invention allow their manufacturers to save cost of transportation and cost of management and their users to enjoy comfortability.

(5) The absorbent body obtained especially by providing the steps of pneumatical molding and theremal compression enables the absorbent polymer concentration therein to be increased to a level falling within the heretofore unattainable range without a sacrifice of the efficiency of absorption of the absorbent polymer. Thus, the absorbent body can be produce d in an extremely small thickness.

The present invention allows the absorbent body enjoying the characteristic properties mentioned above to be produced by a simple and inexpensive method. The absorbent body of the present invention, therefore, is ideal for use in absorbent commodities in the medical and sanitary fields such as, for example, sanitary napkins, disposable diapers, pads for patients suffering from incontinence, pads for excessively secretive breasts, and medical pads. It is further available for various uses requiring retention or absorption of water such as, for example, materials for keeping raw foodstuffs in fresh conditions, agricultural/horticultural water-retaining materials, and industrial water-absorbing materials.

BRIEF DESCRIPTION OF THE DRAWING

FIG. 1 is an electron microscopic photograph of the absorbent material of this invention.

EXPLANATION OF THE PREFERRED EMBODIMENT

Figure 2:
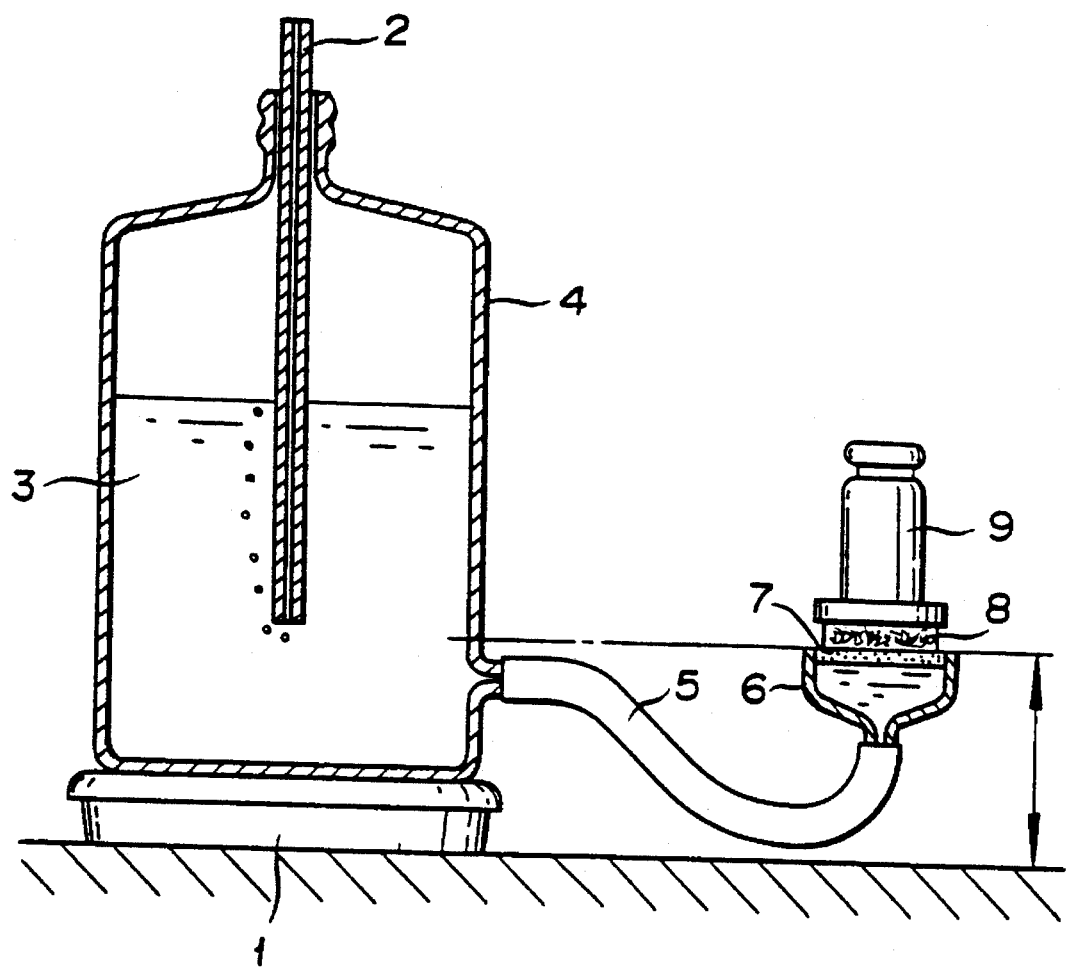
FIG. 2 is a schematic cross section illustrating an apparatus to be used in this invention for the determination of capacity for absorption of liquid under pressure.

The absorbent polymer for use in the present invention is only required to possess an ability to absorb water as a general condition. The .absorbent polymers which are effectively usable herein include (cross-linked) polymers of water-soluble ethylenically unsaturated monomers having (meth)acrylic acid or a salt thereof as a main component and optionally incorporating therein a cross-linking agent, cross-linked derivatives of polyethylene oxide, polyvinyl pyrrolidone, sulfonated polystyrene, and polyvinyl pyridine, saponified starch-poly(meth)acrylonitrile graft copolymers, starch-poly(meth)acrylic acid [poly(meth)acrylate] graft copolymers (and cross-linked derivatives thereof), starch-poly(meth)acrylic ester graft copolymers (and cross-linked derivatives thereof), and hydrolyzed starch-poly-(meth)acrylic ester graft copolymers, for example. Among other absorbent polymers cited above, the (cross-linked) polymers of water-soluble ethylenically unsaturated monomers having acrylic acid or an acrylate as a main component, preferably cross-linked polymers of acrylic acid (and acrylates), prove to be particularly preferable. The absorbent polymer may be produced by any of the methods available at all for the purpose. It is allowable to use two or more species of such absorbent polymers. The absorbent polymer is substantially dry particles which are capable of absorbing not less than 5 g, more preferably 20 to 80 g, and most preferably 35 to 60 g, of physiological saline solution per g of the absorbent polymer. The absorbent polymer generally by nature contains water to some extent. The expression "substantially dry" as used herein means the state in which the individual particles of the absorbent polymer are incapable of mutually adhering by virtue of viscosity under a normal atmosphere. The shapes which the absorbent polymer particles for effective use herein are allowed to assume include beads, pellets, randomly shaped particles, foamed particles, and other forms of powder, and fibers. These particles may be either simple particles or agglomerates. These particles are allowed to have a cross-link density gradient in the surface regions thereof. In the case of an absorbent polymer powder, the particles thereof have a weight average diameter in the range of from 10 to 1,000 microns, preferably from 100 to 700 microns. The synthetic pulp to be used in the present invention is known in the art For example, see "Pulp, Synthetic," Kirk-Othmer, Encyclopedia of Chemical Technology, 3rd Ed.(New York:1982), Vol. 19, pp. 420–435. The pulps are very fine, highly branched, discontinuous fibrils made from thermoplastic resins. Their visual appearance and dimensions closely resemble those of wood pulp. The thermoplastic resins which are effectively usable herein for the production of the synthetic pulp include polyolefins, polyesters, polyacrylonitrile, and other hydrophobic thermoplastic resins, for example. Among other thermoplastic resins mentioned above, polyolefins of one or more α-olefins selected from the group consisting of polyethylene, polypropylene, ethylene-propylene copolymer, ethylene-1-butene copolymer, propylene-1-butene copolymer, and ethylene-4-methyl-1-pentene copolymer prove to be particularly preferable in respect that they are capable of notably improving hydrophilicity. Methods available for the production of the synthetic pulp from the thermoplastic resin are disclosed in JP-A-47-21,898(1972), JP-A-47-32,133(1972), JP-A-3-180,504(1991), JP-A-3-180,505(1991), and JP-A-52-47,049(1977), for example. Typical examples of the synthetic pulp are a proprietary product of Mitsui Petrochemical Co., Ltd. marketed under product code of "SWP", a proprietary product of E. I. du Pont de Nemours & Company marketed under trademark designation of "PULPULS", and a proprietary product of Hercules incorporated marketed under trademark designation of "PULPEX."

The method for the production of the absorbent material of this invention is characterized by mixing 100 parts by weight of the absorbent polymer with 1 to 80 parts by weight, preferably 1 to 30 parts by weight, of the synthetic pulp in the presence of 1 to 40 parts by weight, preferably 5 to 35 parts by weight, of water. Owing to the presence of the stated amount of water in process of the mixture, the absorbent polymer particles are softened in their surface regions and the synthetic pulp in a highly ramified form is caused to adhere to the absorbent polymer in such a manner as to enclose it. As a result, various effects are manifested as described specifically hereinbelow. The amount of the water newly added to the absorbent polymer is as described above. If the amount of the water is less than 1 part by weight, the effects of this invention are not attained because the synthetic pulp is not enabled to cover the surface of the absorbent polymer and solidify the absorbent polymer. Conversely, if this amount exceeds 40 parts by weight, the disadvantage arises that the absorbent material is deficient in the capacity for absorption of a liquid and requires an extra work of drying. Optionally, the water, for the purpose of improving the absorbent material in absorbing characteristics and softness, may incorporate therein a plasticizer for an absorbent polymer such as glycerol or polyethylene glycol, a polyvalent metal salt, a cross-linking agent or a surfactant for a carboxyl group-containing absorbent polymer such as ethylene glycol diglycidyl ether, and a polyhydric alcohol, for example.

The amounts of the synthetic pulp and the water to be used in the present invention relative to the amount of the absorbent polymer may be arbitrarily selected within the aforementioned ranges so as to suit the purpose and use for which the absorbent material is intended. The absorbent material of the present invention can be produced by a simple method of mixing the absorbent polymer particles with the synthetic pulp in the presence of the stated amount of water. Specifically, this production is attained (A) by adding the synthetic pulp to the absorbent polymer particles which have preparatorily absorbed water and mixing them, (B) by mixing the absorbent polymer particles with the synthetic pulp wetted in advance with water, or (C) by dry blending the absorbent polymer particles with the synthetic pulp and then mixing the resultant blend with water, for example. The water can be added in various forms including aqueous solution, drops of solution, steam, and mist (minute droplets of solution), for example. The mixture may be carried out by the use of a kneader, a mixer, a fluidized-bed mixing device, or a screw type rotary mixing device, for example. For the purpose of this mixture, the kind of device is not relevant.

In the produced absorbent material, the synthetic pulp keeps covering the surface of the absorbent polymer particles. This situation is observable under an electron microscope. Though the absorbent material is not particularly restricted in size, it is desired to have an average particle diameter in the range of from 0.05 to 5 mm, preferably from 0.1 to 3 mm The present invention is based on the discovery that the product of mixture of an absorbent polymer with synthetic pulp in the presence of water, when combined with hydrophilic fibers and heated, gives rise to an absorbent article which is soft and excellent in shape-retaining property and exhibits preeminently excellent absorbing characteristics.

The present invention is based on the discovery that the product of mixture of an absorbent polymer with synthetic pulp in the presence of water, when dry mixed with hydrophilic fibers and then thermally compressed to a density in the range of from 0.1 to 1.0 g/cm$^3$, gives rise to a thin absorbent article which is soft and excellent in shape-retaining property and exhibits preeminently excellent absorbing characteristics.

The absorbent body in the present invention basically is a hydrophilic fiber web having absorbent polymer particles dispersed discretely therein and synthetic pulp fused to the surface of the absorbent polymer particles. The absorbent polymer particles may be randomly dispersed or the fiber/absorbent polymer ratio may be arbitrarily varied (fibers may exclusively ocupy certain areas).

The absorbent polymer and the synthetic pulp for use in the present invention are as already described above. The method for the production of the absorbent body of this invention starts with the step of mixing 100 parts by weight of the absorbent polymer with 1 to 80 parts by weight, preferably 1 to 30 parts by weight, of the synthetic pulp in the presence of 1 to 40 parts by weight, preferably 5 to 35 parts by weight, of water. It is important that, in this step, the stated amount of water should be newly present. The mixture of the three components mentioned above may be attained (A) by adding the synthetic pulp to the absorbent polymer particles which have preparatorily absorbed water and mixing them, (B) by mixing the absorbent polymer particles with the synthetic pulp wetted in advance with water, or (C) by dry blending the absorbent polymer particles with the synthetic pulp and thereafter or simultaneously adding water thereto, for example. The water may be added in various forms including aqueous solution, drops of solution, steam, and mist (minute droplets of solution), for example. Optionally, the water, for the purpose of improving the absorbent body in absorbing characteristics and flexibility, may incorporate therein a polyvalent metal salt, a substance such as ethylene glycol diglycidyl ether which serves as a cross-linking agent for a carboxyl group-containing absorbent polymer, a surfactant, and a polyhydric alcohol, for example. The mixture can be carried out by the use of a kneader, a mixer, a fluidized-bed type mixing device, or a screw rotary mixing device, for example. For the sake of this mixtures, the kind of device is not relevant.

Then, the mixture obtained as described above is combined with hydrophilic fibers. The hydrophilic fibers which are effectively usable in the present invention include wood pulp fibers such as mechanical pulp, chemical pulp, semichemical pulp, and dissolved pulp derivable from wood and man-made cellulose fibers such as rayon and acetate, for example. For use in the present invention, these hydrophilic fibers may partly incorporate therein synthetic fibers such as nylon, polyester, and polyolefin. Preferred hydrophilic fibers are wood pulp fibers. The amount of the hydrophilic fibers to be used is in the range of from 10 to 1,000 parts by weight, preferably 10 to 200 parts by weight, based on 100 parts by weight of the absorbent polymer. Various known methods are available for the molding of the resultant mixture in the form of web. For example, the mixture may be molded in the form of web by having this mixture nipped between sheets or mats which are made of hydrophilic fibers. This molding may be otherwise accomplished by uniformly blending the mixture with hydrophilic fibers. The uniform blending can be carried out by metering and supplying an air current containing hydrophilic fibers and an air current containing a mixture of the absorbent polymer with the synthetic pulp simultaneously onto a wire mesh screen. The hydrophilic fibers and the mixture of absorbent polymer are allowed to form a web by their being mixed by dint of the turbulence generated by the two air currents and then deposited on the wire mesh screen.

The web thus prepared is converted into the absorbent body of this invention by virtue of a heat treatment. This heat treatment can be effected as popularly practised (A) by exposing the web to hot air, (B) by heat-treating the web as with an air oven or a (far) infrared heater, (C) by heat-treating the web as kept pressed with a hot roll or a hot press, (D) by subjecting the web to a hot (emboss) roll treatment, or (E) by heating the web with microwaves, for example. The temperature of this heat treatment is in the neighborhood of the softening point of the synthetic pulp which, as a standard, falls in the range of from 60° to 250° C., preferably from 100° to 200° C. The absorbent body obtained by the present invention is preferable to have a basis weight in the range of from 0.01 to 0.15 g/cm$^2$, preferably from 0.015 to 0.1 g/cm$^2$.

The web may be otherwise produced by first metering and supplying an air current containing hydrophilic fibers and an air current containing the mixture of the absorbent polymer with the synthetic pulp simultaneously onto a wire screen thereby causing the hydrophilic fibers and the absorbent polymer mixture to be mixed by dint of the turbulence generated by the two air currents. Alternatively, the mixture may be carried out in an independent mixing chamber in advance of the pneumatic molding of the mixture in the form of a sheet.

The mixture obtained as described above is pneumatically molded in the form of a web. The web in this invention is molded by the use of an ordinary device manufactured exclusively for use in the pneumatic molding of a hydrophilic fiber web. The web is produced by causing the mixture prepared as described above to be deposited on the wire mesh screen. The desired mixed web of the hydrophilic fibers with the absorbent polymer-synthetic fiber mixture is produced by incorporating desired amounts of the absorbent polymer and the synthetic pulp mixture into an air current containing hydrophilic fibers.

In the next step, the web prepared in the last step is thermally compressed to a density in the range of from 0.05 to 1.0 g/cm$^3$, preferably from 0.1 to 0.5 g/cm$^3$, to produce the absorbent body of this invention. When the absorbent body is compressed to a density of at least 0.05 g/cm$^3$, the matrix composed of absorbent polymer-synthetic pulp-hydrophilic fibers is notably improved in absorbing characteristics, wet stability, and flexibility and the absorbent polymer is markedly improved in efficiency of absorption. The thermal compression is fulfilled by passing the web through the gap intervening between opposed hot rolls which are adjusted to give rise to an absorbent article of a desired density. The hot rolls to be used in this thermal compression may be selected from among those cited above. Besides the hot rolls, the known methods and devices cited above are also available for the thermal compression. The heating temperature and the basis weight of the aborbent body are as already described above. The absorbent body optionally for the purpose of acquiring improved flexibility, may be furnished with such a multiplicity of linear slits as to be short of impairing absorbing characteristics.

Now, the present invention will be described below with reference to working examples. Wherever the term "parts" is used in the referential examples, working examples, and controls cited hereinbelow, it shall be construed as meaning "parts by weight" unless otherwise specified.

(Performance test)

The produced absorbent article was evaluated by the following methods.

1. Capacity for absorption under pressure

By the use of an apparatus which, as illustrated in FIG. 2, comprised a container 4 mounted on a balance 1, provided with an ambient air absorbing pipe 2, and containing a 0.9% physiological saline solution 3 and an inverted funnel 6 communicating with the container 4 via a conduit 5 and provided in the top part thereof with a glass filter 7, this property was determined by setting a sample 8 of a given absorbent article cut in advance in a circle 5.5 cm in diameter on the filter 7, keeping the circular sample 8 under a load of 30 g/cm$^2$ exerted by a weight 9 for 30 minutes, and measuring the amount of the physiological saline solution absorbed by the absorbent article (g/g) during the standing under the load.

2. Ratio of exfoliation of absorbent polymer

This property was determined by keeping a sample, 2 cm×4 cm, of a given absorbent article for 10 minutes in 100 cc of a physiological saline solution held in a beaker having an inner volume of 100 cc and kept stirred at a rate of 100 rpm with a stirrer 45 mm in diameter, removing the sample from the beaker,weighing the absorbent polymer fallen off the sample into the physiological saline solution during the 10 minutes'standing in the stirred solution, and calculating the amount of exfoliation of the absorbent polymer in accordance with the following formula.

Amount of exfoliation (%)={(Amount of polymer (g) fallen off)/(Amount of polymer (g) in original absorbent article)}×100

EXAMPLE 1

An absorbent material (1) of this invention was obtained by mixing 100 parts by weight of an absorbent polymer having a weight average particle diameter of 400 microns [produced by Nippon Shokubai Co., Ltd. and marketed under trademark designation of "Aqualick CA"] with 7 parts by weight of synthetic pulp [produced by Mitsui Petrochemical Industries, Ltd. and marketed under product code of "SWP UL-415"] with 25 parts by weight of water sprayed to the site of mixture. Election microscopie photograph of absorbent material (1) was shown in FIG. 1.

EXAMPLE 2

An absorbent material (2) of this invention was obtained by following the procedure of Example 1, except that the amount of the synthetic pulp was changed to 25 parts by weight.

EXAMPLE 3

An absorbent material (3) of this invention was obtained by following the procedure of Example 1, except that the amount of the synthetic pulp was changed to 17 parts by weight.

EXAMPLE 4

An absorbent material (4) of this invention was obtained by following the procedure of Example 3, except that the amount of the water was changed to 10 parts by weight.

EXAMPLE 5

The absorbent materials (1) to (4) were severally nipped between opposed tissue papers having a basis weight of 0.0013 g/cm$^2$ and then heat-treated at 150° C. for 5 minutes, to produce absorbent sheets having respectively absorbent polymers fixed between the tissue papers. The absorbent sheets using the absorbent materials (2) and (3) absorbed 0.9% physiological saline solution in respective ratios of 18 g/g and 20 g/g and, after the absorption of the saline solution, showed no discernible exfoliation of polymer.

EXAMPLE 6

The absorbent material (1) was dry mixed with 140 parts by weight of ground pulp and the resultant mixture was molded in the form of web by the use of a batch type pneumatic molding device. The web thus obtained was heat-treated at 150° C. for 10 minutes to produce an absorbent web having the absorbent polymer fixed within the web. The absorbent web absorbed physiological saline solution in a ratio of 16 g/g under a load of 30 g/cm2 and, after the absorption of the physiological saline solution, showed no discernible exfoliation of polymer.

EXAMPLE 7

The absorbent material (4) was nipped between two opposed webs made of 30 parts by weight of ground pulp and then heat-treated at 150° C., to produce an absorbent web having the absorbent polymer fixed between the two pulp webs. The absorbent web absorbed physiological saline solution in a ratio of 12 g/g under a load and, after the absorption of the saline solution, showed no discernible exfoliation of polymer.

REFERENTIAL EXAMPLE 1

A gel hydrated polymer finely divided into particles about 5 mm in diameter was obtained by stirring for polymerization 4,000 parts of an aqueous 37% solution of an acrylate type monomer composed of 74.98 mol % of sodium acrylate, 25 mol % of acrylic acid, and 0.02 mol % of trimethylolpropane triacrylate with 2.0 parts of sodium persulfate and 0.08 part of l-ascorbic acid in an atmosphere of nitrogen. The gel hydrated polymer was dried with a hot air drying device at 150° C., pulverized with a hammer type pulverizing device, and sifted with a 20-mesh metallic gauze to obtain a 20-mesh pass powder (having an average particle diameter of 405 microns). An absorbent polymer A having a secondary cross-linked surface region was obtained by mixing 100 parts of the separated powder with 0.5 part of glycerol, 2 parts of water, and 2 parts of ethyl alcohol and heat-treating the resultant mixture at 210° C. This absorbent polymer A absorbed physiological saline solution in a ratio of 50 g/g.

REFERENTIAL EXAMPLE 2

A gel hydrated polymer finely divided into particles about 5 mm in diameter was obtained by stirring for polymerization 4,000 parts of an aqueous 37% solution of an acrylate type monomer composed of 74.95 mol % of sodium acrylate, 25 mol % of acrylic acid, and 0.05 mol % of trimethylolpropane triacrylate with 2.0 parts of sodium persulfate and 0.08 part of l-ascorbic acid in an atmosphere of nitrogen. The gel hydrated polymer was dried with a hot air drying device at 150° C., pulverized with a hammer type pulverizing device, and sifted with a 20-mesh metallic gauze to obtain an absorbent polymer B (having an average particle diameter of 350 microns) as a 20-mesh pass powder. This absorbent polymer B absorbed physiological saline solution in a ratio of 46 g/g.

REFERENTIAL EXAMPLE 3

An absorbent polymer C having a secondary cross-linked surface region was obtained by mixing 100 parts of the absorbent polymer B obtained in Referential Example 2 with 0.5 part of glycerol, 2 parts of water, and 2 parts of ethyl alcohol and heat-treating the resultant mixture at 210° C. This absorbent polymer C absorbed physiological saline solution in a ratio of 43 g/g.

REFERENTIAL EXAMPLE 4

The absorbent polymer C obtained in Referential Example 3 was classified with 60- to 100-mesh metallic gauzes to separate an absorbent polymer D (having particle diameters of from 250 to 149 microns). This absorbent polymer D absorbed physiological saline solution in a ratio of 42 g/g.

REFERENTIAL EXAMPLE 5

The absorbent polymer C obtained in Referential Example 3 was passed through a 200-mesh metallic gauze to obtain an absorbent polymer E (having particle diameters not exceeding 74 microns) as a 200-mesh pass powder. This absorbent polymer E absorbed physiological saline solution in a ratio of 38 g/g.

REFERENTIAL EXAMPLE 6

A commercially available cross-linked sodium polyacrylate (marketed under trademark designation of "Aquakeep") was classified with 48- to 145-mesh metallic gauzes to separate an absorbent polymer F (having particle diameters of from 297 to 105 microns). This absorbent polymer F absorbed physiological saline solution in a ratio of 55 g/g.

EXAMPLE 8

A web measuring 14 cm×40 cm in area and having a basis weight of 0.047 g/cm$^2$ was obtained by mixing 100 parts by weight of the absorbent polymer A with 25 parts by weight of synthetic pulp (produced by Mitsui Petrochemical Industries, Ltd. and marketed under product code of "SWP UL-415") with 25 parts by weight of water simultaneously added to the site of mixture, dry mixing the resultant mixture with 125 parts by weight of ground pulp in a mixer, and pneumatically molding the produced mixture in the form of web on a wire screen with a batch type pneumatic molding device. An absorbent body (1) of this invention having a density of 0.16 g/cm³ was obtained by compressing the resultant web and heating the compressed web at 150° C. for 10 minutes. This absorbent body (1) was found to have an amount of absorption of physiological saline solution under pressure (applicable similarly hereinbelow) of 16.5 g/g and a ratio of exfoliation of absorbent polymer of 19%.

EXAMPLE 9

An absorbent body (2) of the present invention having a basis weight of 0.051 g/cm² and a density of 0.13 g/cm³ was obtained by following the procedure of Example 8, except that the amount of the water was changed to 32 parts by weight, the amount of the synthetic pulp to 17 parts by weight, and the amount of the ground pulp to 133 parts by weight. The absorbent body (2) had an amount of absorption under pressure of 16.0 g/g and a ratio of exfoliation of absorbent polymer of 22%.

EXAMPLE 10

A web measuring 14 cm×40 cm in area and having a basis weight of 0.042 g/cm² was obtained by mixing 100 parts by weight of the absorbent polymer A with 7 parts by weight of synthetic pulp wetted in advance with 5 parts by weight of water, dry mixing the resultant mixture with 67 parts by weight of ground pulp in a mixer, and pneumatically molding the produced mixture on a wire screen by the use of a batch type pheumatically molding device. An absorbent body (3) of this invention having a density of 0.20 g/cm³ was obtained by compressing the web obtained as described above and heating the compressed web at 150° C. for 10 minutes. The absorbent body (3) had an amount of absorption under pressure of 15.8 g/g and a ratio of exfoliation of absorbent polymer of 20%.

EXAMPLE 11

A web measuring 14 cm×40 cm in area was produced by mixing 100 parts by weight of the absorbent polymer C with 13 parts by weight of synthetic pulp (produced by Mitsui Petrochemical Industries, Ltd. and marketed under product code of "SWP UL-415"), with 20 parts by weight of water simultaneously added to the site of mixture, then dry mixing the resultant mixture with 100 parts by weight of ground pulp in a mixer, and pneumatically molding the produced mixture on a wire screen by the use of a batch type pneumatically molding device. An absorbent body (4) of this invention having a basis weight of 0.054 g/cm² and a density of 0.27 g/cm³ was obtained by interposing tissue papers of a basis weight of 0.0013 g/cm² one each on the upper and lower surfaces of the web and then emboss pressing the superposed composite at 150° C. for 1 minute. This absorbent body (4) had an amount of aborption under pressure of 14.4 g/g and a ratio of exfoliation of absorbent polymer of 6%.

EXAMPLE 12

An absorbent body (5) of the present invention having a basis weight of 0.044 g/cm² and a density of 0.22 g/cm³ was obtained by following the procedure of Example 11, except that the amount of the ground pulp was changed to 66 parts by weight. The absorbent body (5) had an amount of absorption under pressure of 17,3 g/g and a ratio of exfoliation of absorbent polymer of 7%.

EXAMPLE 13

An absorbent body (6) of the present invention having a basis weight of 0.029 g/cm² and a density of 0.30 g/cm³ was obtained by following the procedure of Example 11, except that the amount of the synthetic pulp was changed to 15 parts by weight and the amount of the ground pulp to 34 parts by weight. The absorbent body (6) had an amount of absorption under pressure of 16.3 g/g and a ratio of exfoliation of absorbent polymer of 19%.

EXAMPLE 14

A web measuring 14 cm×40 cm in area obtained by mixing 100 parts by weight of the absorbent polymer C with 12 parts by weight of synthetic pulp (produced by Mitsui Petrochemical Industries, Ltd. and marketed under product code of "SWP UL-415") with 20 parts by weight of water simultaneously added to the site of mixture, dry mixing the resultant mixture with 131 parts by weight of ground pulp in a mixer, and pneumatically molding the produced mixture in the form of web on a wire screen with a batch type pneumatic molding device. An absorbent body (7) of this invention having a basis weight of 0.047 g/cm² and a density of 0.24 g/cm³ was obtained by interposing tissue paper of a basis weight of 0.0013 g/cm² one each on the upper and lower surfaces of the web and then emboss pressing the superposed composite at 150° C. for 1 minute. This absorbent body (7) had an amount of absorption under pressure of 12.5 g/g and a ratio of exfoliation of absorbent polymer of 8%.

EXAMPLE 15

An absorbent body (8) of the present invention having a basis weight of 0.050 g/cm² and a density of 0.25 g/cm³ was obtained by following the procedure of Example 14, except that the amount of the synthetic pulp was changed to 5 parts by weight and the amount of the ground pulp to 100 parts by weight. The absorbent body (8) had an amount of absorption under pressure of 15.3 g/g and a ratio of exfoliation of absorbent polymer of 13%.

EXAMPLE 16

An absorbent body (9) of the present invention having a basis weight of 0.060 g/cm² and a density of 0.30 g/cm³ was obtained by following the procedure of Example 14, except that the amount of synthetic pulp was changed to 23 parts by weight and the amount of the ground pulp to 133 parts by weight. The absorbent body (9) had an amount of absorption under pressure of 13.5 g/g and a ratio of exfoliation of absorbent polymer of 12%.

EXAMPLE 17

An absorbent body (10) of the present invention having a basis weight of 0.070 g/cm² and a density of 0.35 g/cm³ was obtained by following the procedure of Example 14, except the amount of the synthetic: pulp was changed to 24 parts by weight and the amount of the ground pulp to 167 parts by weight. The absorbent body (10) had an amount of absorption under pressure of 12.3 g/g and a ratio of exfoliation of absorbent polymer of 15%.

EXAMPLE 18

An absorbent body (11) of the present invention having a basis weight of 0.044 g/cm$^2$ and a density of 0.33 g/cm$^3$ was obtained by following the procedure of Example 16, except that the amount of the ground pulp was changed to 67 parts by weight. The absorbent body(11) had an amount of absorption under pressure of 14.2 g/g and a ratio of exfoliation of absorbent polymer of 10%.

EXAMPLE 19

A web measuring 14 cm×40 cm in area was obtained by mixing 100 parts by weight of the absorbent polymer D with 13 parts by weight of synthetic pulp (produced by Mitsui Petrochemical Industries, Ltd. and marketed under product code of "SWP UL-415") with 20 parts by weight of 30% by weight of an aqueous solution of polyaluminum chlovide simultaneously added to the site of mixture, dry mixing the resultant mixture with 100 parts by weight of ground pulp in a mixer, and pneumatically molding the produced mixture in the form of web on a wire screen with a batch type pneumatic molding device. An absorbent body (12) of this invention having a basis weight of 0.042 g/cm$^2$ and a density of 0.21 g/cm$^3$ was obtained by interposing tissue papers of a basis weight of 0.0013 g/cm$^2$ one each on the upper and lower surfaces of the web and then emboss pressing the superposed composite at 150° C. for 1 minute. This absorbent body (12) had an amount of absorption under pressure of 13.2 g/g and a ratio of exfoliation of absorbent polymer of 5%.

EXAMPLE 20

A web measuring 14 cm×40 cm in area was obtained by mixing 100 parts by weight of the absorbent polymer B with 13 parts by weight of synthetic pulp (produced by Mitsui Petrochemical Industries, Ltd. and marketed under product code of "SWP UL-415") with 2.0 parts by weight of 1% by weight of aqueous solution of ethyleneglycol diglycidylether (produced by Nagase Kasei K.K. and marketed under product code Denacol EX-810) simultaneously added to the site of mixture, dry mixing the resultant mixture with 67 parts by weight of ground pulp in a mixer, and pneumatically molding the produced mixture in the form of web on a wire screen with a batch type pneumatic molding device. An absorbent body (13) of this invention having a basis weight of 0.047 g/cm$^2$ and a density of 0.23 g/cm$^3$ was obtained by interposing tissue paper of a basis weight of 0.0013 g/cm$^2$ one each on the upper and lower surfaces of the web and then enboss pressing the superposed composite at 150° C. for 1 minute. This absorbent body (13) was found to have an amount of absorption under pressure of 13.7 g/g and a ratio of exfoliation of absorbent polymer of 3%.

EXAMPLE 21

An absorbent body (14) of the present invention having a basis weight of 0.043 g/cm$^2$ and a density of 0.22 g/cm$^3$ was obtained by following the procedure of Example 15, except that the amount of the synthetic pulp to 7 parts by weight. The absorbent body (14) had an amount of absorption under pressure of 15.3 g/g and a ratio of exfoliation of absorbent polymer of 14%.

EXAMPLE 22

A web measuring 14 cm×40 cm in area was produced by mixing 100 parts by weight of the absorbent polymer C with 13 parts by weight of synthetic pulp (produced by Mitsui Petrochemical Industries, Ltd. and marketed under product code of "SWP UL-415"), with 20 parts by weight of water simultaneously added to the site of mixture, then dry mixing the resultant mixture with 100 parts by weight of ground pulp in a mixer, and pneumatically molding the produced mixture on a wire screen by the use of a batch type pneumatically molding device. An absorbent body (15) of this invention having a basis weight of 0.052 g/cm$^2$ and a density of 0.26 g/cm$^3$ was obtained by interposing tissue papers of a basis weight of 0.002 g/cm$^2$ one each on the upper and lower surfaces of the web and then emboss pressing the superposed composite at 200° C. for 10 seconds. This absorbent body (15) had an amount of aborption under pressure of 14.5 g/g and a ratio of exfoliation of absorbent polymer of 11%.

EXAMPLE 23

A web measuring 14 cm×40 cm in area was produced by mixing 100 parts by weight of the absorbent polymer C with 10 parts by weight of synthetic pulp (produced by Mitsui Petrochemical Industries, Ltd. and marketed under product code of "SWP UL-415"), with 20 parts by weight of water simultaneously added to the site of mixture, then dry mixing the resultant mixture with 133 parts by weight of ground pulp in a mixer, and pneumatically molding the produced mixture on a wire screen by the use of a batch type pneumatically molding device. An absorbent body (16) of this invention having a basis weight of 0.092 g/cm2 and a density of 0.23 g/cm$^3$ was obtained by interposing tissue papers of a basis weight of 0.002 g/cm$^2$ one each on the upper and lower surfaces of the web and then emboss pressing the superposed composite at 150° C. for 10 minutes. This absorbent body (16) had an amount of aborption under pressure of 13.5 g/g and a ratio of exfoliation of absorbent polymer of 29%.

EXAMPLE 24

100 Parts by weight of the absorbent polymer A was mixed with 8 parts by weight of synthetic pulp under adding 20 parts by weight of water. A web was obtained by dry mixing the mixture thus obtained with 70 parts by weight of the ground pulp in a mixer and pneumatically molding the produced mixture onto a wire screen. On one hand, a web comprising 35 parts by weight of ground pulp and 0.7 part by weight of synthetic pulp was prepared and the former web was superposed by two latter webs one each on the upper and lower surfaces of the web to obtain a web measuring 14 cm×40 cm in area and having a basis weight of 0.046 g/cm$^2$. The web thus obtained was emboss pressed at 150° C. for 1 minute to obtain an absorbent body (17) of this invention having a density of 0.22 g/cm$^3$. The absorbent body (17) had an amount of absorption under pressure of 13.5 g/g and a ratio of exfoliation of absorbent polymer of 20%.

EXAMPLE 25

100 Parts by weight of the absorbent polymer D was mixed with 20 parts by weight of synthetic pulp under adding 20 parts by weight of water. A web was obtained by dry mixing the mixture thus obtained with 18 parts by weight of ground pulp in a mixer and pneumatically molding the produced pulp onto a wire screen. An absorbent body (18) of this invention having a basis weight of 0.09 g/cm$^2$ and a density of 0.25 g/cm$^3$ was obtained by interposing tissue paper of a basis weight of 0.0013 g/cm$^2$ one each on the upper and lower surfaces of the web and them emboss pressing the superposed composite at 150° C. for 1 minute. The absorbent body (18) had an amount of absorption under pressure of 18.0 g/g and a ratio of exfoliation of absorbent polymer of 35%.

EXAMPLE 26

A web measuring 14 cm×40 cm in area and having a basis weight of 0.052 g/cm$^2$ was produced by mixing 100 parts by weight of the absorbent polymer A with 13 parts by weight of synthetic pulp (produced by Mitsui Petrochemical Industries, Ltd. and marketed under product code of "SWP UL-415"), with 10 parts by weight of water simultaneously added to the site of mixture, then superposing two webs comprising 33 parts by weight of ground pulp one each on the upper and lower surfaces of the resultant mixture. An absorbent body (19) of this invention having a density of 0.17 g/cm$^3$ was obtained by compressing the web obtained as described above and heating the compressed web at 150° C. for 1 minute. This absorbent body (19) had an amount of aborption under pressure of 12.5 g/g and a ratio of exfoliation of absorbent polymer of 33%.

EXAMPLE 27

A web measuring 14 cm×40 cm in area was produced by mixing 100 parts by weight of the absorbent polymer C with 20 parts by weight of synthetic pulp (produced by Mitsui Petrochemical Industries, Ltd. and marketed under product code of "SWP UL-415"), with 20 parts by weight of water simultaneously added to the site of mixture, then dry mixing the resultant mixture with 60 parts by weight of ground pulp in a mixer, and pneumatically molding the produced mixture on a wire screen by the use of a batch type pneumatically molding device. An absorbent body (20) of this invention having a basis weight of 0.048 g/cm$^2$ and a density of 0.16 g/cm$^3$ was obtained by seting 30 perts by weight of ground pulp on one surface of the web and interposing tissue papers of a basis weight of 0.0013 g/cm$^2$ one each on the upper and lower surfaces of the web and then passing between hot rollers to heat at 200° C. for 20 seconds. This absorbent body (20) had an amount of aborption under pressure of 12.2 g/g and a ratio of exfoliation of absorbent polymer of 14%.

EXAMPLE 28

A web measuring 14 cm×40 cm in area was produced by mixing 100 parts by weight of the absorbent polymer E with 13 parts by weight of synthetic pulp (produced by Mitsui Petrochemical Industries, Ltd. and marketed under product code of "SWP UL-415"), with 20 parts by weight of 30% by weight of an aqueous solution of polyaluminum chloride simultaneously added to the site of mixture, then dry mixing the resultant mixture with 100 parts by weight of ground pulp in a mixer, and pneumatically molding the produced mixture on a wire screen by the use of a batch type pneumatically molding device. An absorbent body (21) of this invention having a basis weight of 0.042 g/cm$^2$ and a density of 0.21 g/cm$^3$ was obtained by interposing tissue papers of a basis weight of 0.0013 g/cm$^2$ one each on the upper and lower surfaces of the web and then emboss pressing the superposed composite at 150° C. for 1 minute. This absorbent body (21) had an amount of aborption under pressure of 12.1 g/g and a ratio of exfoliation of absorbent polymer of 12%.

EXAMPLE 29

An absorbent body (22) of the present invention having a basis weight of 0.049 g/cm$^2$ and a density of 0.24 g/cm$^3$ was obtained by following the procedure of Example 28, except that the absorbent polymer F was used instead of the absorbent polymer E. The absorbent body (22) had an amount of absorption under pressure of 13.9 g/g and a ratio of exfoliation of absorbent polymer of 17%.

EXAMPLE 30

A web measuring 14 cm×40 cm in area was produced by mixing 100 parts by weight of the absorbent polymer C with 33 parts by weight of synthetic pulp (produced by Mitsui Petrochemical Industries, Ltd. and marketed under product code of "SWP UL-415"), with 20 parts by weight of water simultaneously added to the site of mixture, then dry mixing the resultant mixture with 100 parts by weight of ground pulp in a mixer, and pneumatically molding the produced mixture on a wire screen by the use of a batch type pneumatically molding device. An absorbent body (23) of this invention having a basis weight of 0.048 g/cm$^2$ and a density of 0.24 g/cm$^3$ was obtained by interposing tissue papers of a basis weight of 0.0013 g/cm$^2$ one each on the upper and lower surfaces of the web and then emboss pressing the superposed composite at 150° C. for 1 minute. This absorbent body (23) had an amount of aborption under pressure of 10.2 g/g and a ratio of exfoliation of absorbent polymer of 17%.

EXAMPLE 31

A web measuring 14 cm×40 cm in area was produced by mixing 100 parts by weight of the absorbent polymer C with 66 parts by weight of synthetic pulp (produced by Mitsui Petrochemical Industries, Ltd. and marketed under product code of "SWP UL-415"), with 20 parts by weight of water simultaneously added to the site of mixture, then dry mixing the resultant mixture with 100 parts by weight of ground pulp in a mixer, and pneumatically molding the produced mixture on a wire screen by the use of a batch type pneumatically molding device. An absorbent body (24) of this invention having a basis weight of 0.056 g/cm$^2$ and a density of 0.28 g/cm$^3$ was obtained by interposing tissue papers of a basis weight of 0.0013 g/cm$^2$ one each on the upper and lower surfaces of the web and then emboss pressing the superposed composite at 150° C. for 1 minute. This absorbent body (24) had an amount of aborption under pressure of 8.8 g/g and a ratio of exfoliation of absorbent polymer of 5%.

CONTROL 1

A web measuring 14 cm×40 cm in area was obtained by dry mixing 100 parts by weight of the absorbent polymer C with 100 parts by weight of ground pulp in a mixer and then pneumatically molding the resultant mixture on a wire screen by the use of a batch type pneumatically molding device. An absorbent body (1) for comparison having a basis weight of 0.043 g/cm$^2$ and a density of 0.17 g/cm$^3$ was obtained by interposing tissue papers of a basis weight of 0.0013 g/cm$^2$ one each on the upper and lower surfaces of the web obtained as described above and then emboss pressing the superposed composite at 150° C. for 1 minute. The absorbent body (1) for comparison had an amount of absorption under pressure of 12.3 g/g and a ratio of exfoliation of absorbent polymer of 76%.

CONTROL 2

A web measuring 14 cm×40 cm in area was obtained by dry mixing 100 parts by weight of the absorbent polymer C with 13 parts by weight of synthetic pulp (marketed under product code of "UL 415") and 100 parts by weight of ground pulp in a mixer and then pneumatically molding the resultant mixture on a wire screen by the use of a batch type pneumatically molding device. An absorbent body (2) for comparison having a basis weight of 0.049 g/cm$^2$ and a density of 0.25 g/cm$^3$ was obtained by interposing tissue papers of a basis weight of 0.0013 g/cm$^2$ one each on the upper and lower surfaces of the web and then emboss pressing the superposed composite at 150° C. for 1 minute. The absorbent body (2) for comparison had an amount of absorption under pressure of 10.9 g/g and a ratio of exfoliation of absorbent polymer of 53%.

CONTROL 3

A web measuring 14 cm×40 cm in area having a basis weight of 0.048 g/cm$^2$ was obtained by mixing 100 parts by weight of the absorbent polymer C with 25 parts by weight of synthetic pulp under adding 60 parts by weight of water, dryixing the resultant mixture with 100 parts by weight of ground pulp in a mixer and then pneumatically molding the resultant mixture on a wire screen by the use of a batch type pneumatically molding device. An absorbent body (3) for comparison having a density of 0.25 g/cm$^3$ was obtained by compressing the resultant web at 150° C. for 3 minutes. The absorbent body (3) for comparison had an amount of absorption under pressure of 9.9 g/g and a ratio of exfoliation of absorbent polymer of 30%.

CONTROL 4

A web measuring 14 cm×40 cm in area having a basis weight of 0.048 g/cm$^2$ was obtained by dry mixing 100 parts by weight of the absorbent polymer C with 25 parts by weight of synthetic pulp ("UL 415") under adding 0.5 parts by weight of water, dry mixing the resultant mixture with 100 parts by weight of ground pulp in a mixer and then pneumatically molding the resultant mixture on a wire screen by the use of a batch type pneumatically molding device. An absorbent body (4) for comparison having a density of 0.25 g/cm$^3$ was obtained by compressing the resultant web at 150° C. for 1 minute. The absorbent body (4) for comparison had an amount of absorption under pressure of 11.9 g/g and a ratio of exfoliation of absorbent polymer of 60%.

EXAMPLE 32

A disposable diaper comprising a liquid-pervious polypropylene top sheet, two tissue papers, a section (9 cm×35 cm in area and 15 g in weight) of the absorbent body (1) of this invention, a liquid-impervious polyethylene back sheet containing leg gathers, and two tape fasteners was manually assembled by tying the components with a double-faced adhesive tape. The total weight of the diaper was 33 g.

The diaper was tried on a one-year old infant (weighing 10 kg) in comparison with a commercially available diaper (total weight 50 g). The diaper using the absorbent article of this invention exhibited a preeminently excellent shape-retaining property after absorption of urine and suffered from leakage only slightly.

EXAMPLE 33

An absorbent body (4) having a basis weight of 0.054 g/cm$^2$ and a density of 0.27 g/cm$^3$ was obtained by giving grooves of 5 mm in length and 0.5 mm of width in an interval of 7 mm in length and 10 mm of width by a cutter. The absorbent body (4) thus obtained had an amount of absorption under pressure of 14.2 g/g and a ratio of exfoliation of absorbent polymer of 10%. Garlay hardness value (JIS L-1096) before forming the grooves was 1.5 (mgf), but after forming the grooves it was 0.5 (mgf)(when the grooves was measured vertically in a bending direction) and 1.0 (mgf)(when the groove was measured parallely in a bending direction).

What is claimed is:

1. A method for the production of an absorbent material which comprises making 100 parts by weight of an absorbent polymer with 1 to 80 parts by weight of synthetic pulp, said synthetic pulp being a fine, branched discontinuous fibrous material made from thermoplastic resin, in the presence of 1 to 40 parts by weight of water.

2. A method according to claim 1, wherein said absorbent polymer is a cross-linked polymer of a water-soluble ethylenic monomer having acrylic acid or a salt thereof as a main component thereof.

3. A method according to claim 1, wherein the amount of said synthetic pulp is in the range of from 1 to 30 parts by weight, based on 100 parts by weight of said absorbent polymer.

4. A method according to claim 1, wherein said absorbent polymer is a particulate substance having a weight average diameter in the range of from 10 to 1,000 microns.

5. A method according to claim 2, wherein said absorbent polymer has an amount of absorption of physiological saline solution of not less than 5 g/g.

6. A method according to claim 1, wherein said absorbent polymer is a particulate substance having a weight average particle diameter in the range of from 100 to 700 microns.

7. A method for the production of an absorbent body which comprises mixing 100 parts by weight of an absorbent polymer with 1 to 80 parts by weight of synthetic pulp in the presence of 1 to 40 parts by weight of water, combining the resultant mixture with 10 to 1,000 parts by weight of hydrophilic fibers, based on 100 parts by weight of said absorbent polymer, to form a web and heat-treating the web.

8. A method according to claim 7, wherein said absorbent polymer is a cross-linked polymer of a water-soluble ethylenic monomer having acrylic acid or a salt thereof as a main component thereof.

9. A method according to claim 7, wherein the amount of said synthetic pulp is in the range of from 1 to 30 parts by weight, based on 100 parts by weight of said absorbent polymer.

10. A method according to claim 7, wherein the amount of said hydrophilic fibers is in the range of from 10 to 200 parts by weight, based on 100 parts by weight of said absorbent polymer.

11. A method according to claim 7, wherein the temperature of heating is in the range of from 60° to 250° C.

12. A method according to claim 7, wherein the density of said absorbent body is at least 0.05 g/cm$^3$.

13. A method according to claim 7, wherein the basis weight of said absorbent body is in the range of from 0.01 to 0.15 g/cm$^2$.

14. A method according to claim 7, wherein said absorbent polymer is a particulate substance having a weight average particle diameter in the range of from 10 to 1,000 microns.

15. A method according to claim 7, wherein said synthetic pulp is polyolefin pulp.

16. A method for the production of an absorbent body which comprises (a) a step of mixing 100 parts by weight of an absorbent polymer with 1 to 80 parts by weight of synthetic pulp in the presence of 1 to 40 parts by weight of water, (b) a step of dry mixing the mixture obtained in the step of (a) with 10 to 1,000 parts by weight of hydrophilic fibers based on 100 parts by weight of said absorbent polymer, (c) a step of pneumatically molding the mixture obtained in the step of (b) in the form of web, and (d) a step of thermally compressing the web of the step of (c) to a density in the range of from 0.1 to 1.0 g/cm$^3$.

17. A method according to claim 16, wherein said absorbent polymer is a cross-linked polymer of a water-soluble ethylenic monomer having acrylic acid or a salt thereof as a main component thereof.

18. A method according to claim 16, wherein the amount of said synthetic pulp is in the range of from 1 to 30 parts by weight based on 100 parts by weight of said absorbent polymer.

19. A method according to claim 16, wherein the amount of said hydrophilic fibers is in the range of from 10 to 200 parts by weight based on 100 parts by weight of said absorbent polymer.

20. A method according to claim 16, wherein the temperature of thermally compressing is in the range of from 60° to 250° C.

21. A method according to claim 16, wherein said absorbent body has a weight per unit area in the range of from 0.01 to 0.15 g/cm$^2$.

22. A method according to claim 16, wherein said absorbent polymer is a particulate substance having a weight average particle diameter in the range of from 10 to 1,000 microns.

23. A method according to claim 16, wherein said synthetic pulp is a fine, branched, discontinuous fibrous material made from thermoplastic resin.

* * * * *